United States Patent [19]

Keilman et al.

[11] Patent Number: 4,717,668
[45] Date of Patent: Jan. 5, 1988

[54] PLASTIC ROLLER BOTTLE FOR SUSPENSION CULTURES

[75] Inventors: Michael R. Keilman, Mundelein; Ronald P. Symbol, Round Lake Beach, both of Ill.

[73] Assignee: Baxter Travenol Laboratories, Inc., Deerfield, Ill.

[21] Appl. No.: 940,889

[22] Filed: Dec. 12, 1986

[51] Int. Cl.[4] .............................................. C12M 1/24
[52] U.S. Cl. .................................. 435/296; 435/292; 435/287; 435/286; 215/DIG. 3; 215/307
[58] Field of Search ............... 435/284, 286, 296, 312; 206/0.5, 569, 438, 439; 215/307, 1 R, 11 E, 11 R, DIG. 3; 220/71-75, 83, DIG. 14, DIG. 22

[56] References Cited

U.S. PATENT DOCUMENTS

| | | | |
|---|---|---|---|
| 1,626,425 | 4/1927 | Pelsue | 215/11 C |
| 3,223,595 | 12/1965 | Brewer . | |
| 3,540,700 | 11/1970 | Freedman | 435/312 X |
| 3,589,983 | 6/1971 | Holderith et al. | 435/296 |
| 3,875,000 | 4/1975 | Kaneda | 435/284 X |
| 3,893,887 | 7/1975 | Smith et al. | 435/284 X |
| 3,904,059 | 9/1975 | Bellamy, Jr. et al. | 215/DIG. 3 X |
| 4,036,698 | 7/1977 | Bush et al. . | |
| 4,140,162 | 2/1976 | Gajewski . | |
| 4,166,768 | 9/1979 | Tolbert et al. . | |
| 4,178,209 | 12/1979 | Tolbert et al. . | |
| 4,351,900 | 9/1982 | Lemonnier . | |
| 4,611,643 | 9/1986 | Beebe et al. | 141/311 R |

Primary Examiner—Larry Jones
Attorney, Agent, or Firm—Paul C. Flattery; Bradford R. L. Price; Garrettson Ellis

[57] ABSTRACT

A plastic roller bottle is provided for suspension cultures for bacteriology or other cell growth or maintenance. The roller bottle comprises a closed bottle defining a longitudinal axis and having flexible plastic walls. Aseptically sealable means for access into the closed body are provided as well. A plurality of spaced reinforcement rings are defined in the flexible plastic walls about the longitudinal axis, to cause the body to normally retain a predetermined, generally cylindrical shape. The flexible plastic walls, apart from the rings, are made of a plastic formulation, and are of a thickness such that the oxygen and carbon dioxide diffusion which takes place through said walls is sufficient to support desired biochemical culturing processes taking place within the roller bottle without venting.

11 Claims, 2 Drawing Figures

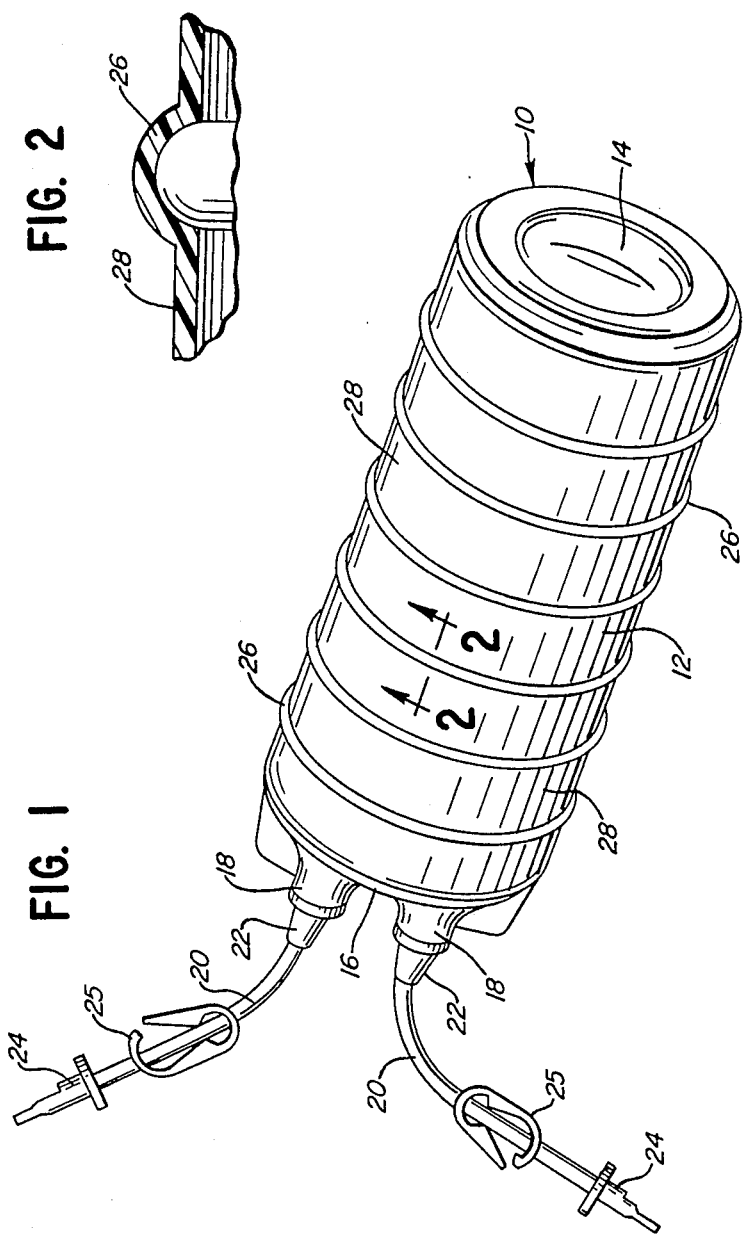

PLASTIC ROLLER BOTTLE FOR SUSPENSION CULTURES

TECHNICAL FIELD

In the culturing of bacteria and other cells, it is common for the cells to be free floating in liquid media. To avoid stagnation, the culture container is often agitated either by shaking or rolling, with conventional apparatus for both processes being commercially available. Conventional culture bottles are made of glass or plastic. Particularly when the culturing process is aerobic, the container must be vented, for example through the neck of a bottle which is closed with a cotton ball.

Generally, the various means for venting of a conventional culture bottle provide a potential source of contamination of the culture. This has been a continuous problem in the field. Furthermore, particular difficulties are encountered if one wishes to vent a roller type culture bottle, which lies horizontally upon a roller mechanism to continuously agitate the contents of the bottle by rolling it about its longitudinal axis. In this circumstance, as well as in all agitation situations, the cotton wad in a bottle mouth can be wetted by the culture solution, increasing the chance for contamination passing from the air through the cotton into the culture media.

Additionally, glass bottles are, of course breakable and heavy, and expensive enough that they generally need to be washed and reused, which is an inconvenient procedure to administer, and labor intensive.

In accordance with this invention a potentially disposable plastic roller bottle is provided, which does not require a mechanical vent to provide high enough levels of oxygen and carbon dioxide transfer into and out of the container for aerobic culturing processes. Since a mechanical vent is not required, the container can be completely sealed under aseptic conditions during the culturing process, greatly reducing the chances of contamination of the culture. Also, the plastic roller bottle of this invention is of much lighter weight than glass containers, and cheap enough to manufacture that it can be disposed of after use rather than cleaned, sterilized, and reused. Furthermore, the roller bottle of this invention can be used in existing machines for providing agitation to culture media, either roller-type machines or, if desired, shaker machines.

DESCRIPTION OF THE INVENTION

By this invention a plastic roller bottle is provided for suspension cultures. The roller bottle comprises a closed body defining a longitudinal axis and having flexible plastic walls. Aseptically sealable means for access into the closed body are also provided, for example one or more flexible, thermoplastic access tubes communicating through the closed body at one end thereof with the access tube having a free end which is sealed to sterile connector means, which may be of a conventional design.

A plurality of spaced reinforcement rings may be defined in the flexible plastic walls about the longitudinal axis, to cause the body to normally retain a predetermined, generally cylindrical shape. The reinforcement rings may be formed integrally with the remainder of the flexible plastic walls. For example, the rings may simply constitute in cross section an outward convolution of the bag wall, permitting a design of roller bottle which may be blow molded. Alternatively, the rings may be solid and of greater thickness relative to the rest of the container wall, with the container body being made by injection molding.

The flexible plastic walls, particularly apart from the rings, may be made of a plastic formulation and may be of a thickness such that both oxygen and carbon dioxide diffuse through the container walls to a degree sufficient to permit aerobic cell culturing to take place in the bottle even though no mechanical vent is provided. Transfer of carbon dioxide out of the container and diffusion of oxygen into the container can take place through the container walls at a rate sufficient to permit aerobic culturing.

Preferably, the oxygen and carbon dioxide permeability of the flexible plastic walls provide an oxygen diffusion of at least 40 cc and a carbon dioxide diffusion of at least 150 cc per square meter per hour through said plastic walls, apart from said rings (the gases being measured at 1 Atm. and 25° C.). In combination with this, it is also preferred for about 400 to 1000 square centimeters of said plastic walls, apart from said rings, to be present in each bottle. This can provide sufficient oxygen and carbon dioxide diffusion capability to a container of about 1 to 2 liter volume.

It is generally preferred for the plastic material of which the bottle of this invention is made to be of the type described in U.S. Pat. No. 4,140,162. Specifically, the plastic used herein may be a polymeric blend, typically free of liquid plasticizers, of (1) 20 parts of a polypropylene polymer having a melt flow of about 2 with a small amount of copolymerized ethylene (Rexene, sold by Dart Industries, Inc.). (2) 60 parts by weight of a poly (ethylene-butylene)-polystyrene copolymer having a molecular weight of about 100,000, with a middle ethylene-butylene block comprising about 70 percent by weight of the polymer, and with terminal polystyrene blocks, and further containing an antioxidant (Kraton G 1660, sold by the Shell Chemical Company); and (3) 20 parts by weight of a poly(ethylene-vinyl acetate) copolymer having about 28 weight percent of vinyl acetate units. The material is further described in Example 2 of U.S. Pat. No. 4,140,162, which is incorporated herein by reference.

Materials such as the one described above have been found to exhibit a desirable rate of oxygen and carbon dioxide diffusion, and have been used in other flexible, collapsible bag products for that purpose, for example platelet storage bags. It is preferred for the bottle of this invention, to have plastic walls, apart from said rings, having a thickness of 0.012 to 0.04 in. to provide an optimum combination of physical strength coupled with high oxygen and carbon dioxide diffusion characteristics.

The reinforcement rings may typically be uniformly spaced along the length of the generally cylindrical body, being present in sufficient number to provide a significant increase in rigidity to a container which would otherwise tend to be significantly more collapsible and flaccid. Accordingly, the bottle of this invention, while having thin, flexible walls apart from said rings, exhibits sufficient rigidity so that it can be filled with culture media, and continuously agitated, for example on a conventional media bottle rolling machine. Thus, the bottles of this invention may be designed to replace glass or other rigid containers without any significant modification of the expensive processing apparatus in the cell culturing laboratory. In face, the bottles of this invention may be used interchangeably and simultaneously with glass or other rigid containers for culturing of bacteria, cell cultures, or other microorganisms, particularly where aerobic culturing is desired.

Additionally, the bottle of this invention may be used to provide culture which have a very high likelihood of being free of contaminations, since the bottle is not vented in any way, particularly when access to the bottle is controlled by a sterile connector of any effective kind, for example one of those as described in U.S. Pat. No. 4,611,643.

Preferably, the clear, flexible plastic formulation desirably used to make the container of this invention comprises from 10 to 40 percent by weight of a polyolfin consisting essentially of polypropyllene units; from 40 to 85 percent by weight of a block copolymer, having thermoplastic rubber characteristics, consisting essentially of (1) a central block, comprising 50 to 85 percent by weight of the copolymer molecule, of a rubbery olefin polymer of generally equal proportions of ethylene and butylene units, and (2) terminal blocks of polystyrene; and from 10 to 40 percent by weight of a softening agent comprising poly(ethylene-vinyl acetate) consisting essentially of 28 to 35 percent by weight of vinyl acetate units, such plastic formulation being essentially free of liquid plasticizers.

DESCRIPTION OF THE DRAWINGS

In the drawings,

FIG. 1 is a perspective view of the sealed bottle of this invention;

FIG. 2 is a sectional view taken along line 2—2 of FIG. 1.

DESCRIPTION OF SPECIFIC EMBODIMENT

Referring to the drawings, plastic bottle 10 is disclosed having a closed body 12 with a closed end 14 and an opposed end 16 defining a pair of ports 18. An optional sampling port or ports may also be added. Body 12 may be manufactured by blow molding from a molten plastic parison using conventional technology. Flexible thermoplastic plastic tubing 20 may be sealed in ports 18 by means of adaptor 22, with tubing 20 being terminated at its outer end with a sterile connector member 24, for example a sterile connector of the design disclosed in U.S. Pat. No. 4,611,643, or any other design of sterile connector. Conventional clamps 25 are provided to control flow through tubes 20.

As stated above, closed body 12 may be made of a plastic blend that permits high diffusion rates of oxygen and carbon dioxide through its walls, for example the specific plastic formulation previously described. Body 12 also exhibits a plurality of spaced reinforcement rings 26, which may be conventionally formed during the blow molding process. Rings 26 provide increased rigidity to the cylindrical body, permitting it to function as a relatively rigid bottle rather than as a flexible, collapsible container, despite the inherent flexibility of the thin plastic wall material 28 of the areas of body 12 spaced from reinforcement rings 26.

Specifically, the plastic wall portions 28 which are apart from ribs 26 may exhibit an oxygen diffusion of about 54 cc. and a carbon dioxide diffusion of about 208 cc. per square meter per hour of area 28 of the plastic walls 28, apart from such rings. The conditions oxygen and carbon dioxide diffusion are as described above.

In combination with this, body 12 may have an overall area of plastic walls 28 of about 850 to 210 square centimeters, depending on the volume desired for bottle 10, which provides a significant amount of oxygen and carbon dioxide diffusion capability through the walls of such a bottle, to permit aerobic culturing processes within bottle 14 without venting.

Furthermore, added diffusion may take place through the plastic defining end surfaces 14, 16, although they may for structural reasons be thicker than wall areas 28, and thus provide less diffusion per square centimeter. Additionally, some diffusion can take place through the surfaces of rings 26 themselves, especially with rings 26 of arcuate, relatively thin configuration as shown herein rather than in an alternate configuration where the rings 26 define a solid, thick cross section, as may be the case in an injection molded bottle in accordance with this invention which otherwise substantially corresponds to bottle 10 as shown herein.

Specifically, plastic wall 28, apart from rings 26, may have a thickness on the order of 0.015 to 0.025 inch. In blow molded containers, the wall thickness of ribs 26 will generally be no thicker than the thickness of wall portions 28 and usually slightly thinner, while some area of end portions 14, 16 tends to be of greater wall thickness as an artifact of the blow molding process. However, such is not deemed to be a necessary aspect of the invention.

The bottle of this application is proportioned to be useable in conventional roller type culturing apparatus for providing continuous agitation, aerobic culturing of microorganisms under conditions where the risk of contamination is reduced to a very low level. The bottle of this invention may also be used for culturing and storing microorganisms under quiet conditions as well, or it may be used for culturing in a shaking apparatus if desired. The bottle of this invention may also be used to make sterile connection with an Apheresis kit, to receive a blood fraction from such a kit for culturing or storing. Apheresis kits are commercially available from the Fenwal division of Travenol Laboratories, Deerfield, Ill.

For use of the bottle of this invention, one may preferably make a sterile connection, through one of conventional sterile connectors 24, with a source of culture material. If desired, the nutrient media into which the culture material is innoculated may be stored within bottle 10 as it is provided to the user, with bottle 10 being sterilized in an appropriate manner, for example steam sterilized. Alternatively, nutrient media may be introduced into the sterilized system through one of the sterile connectors 24 and tubes 20. In the specific embodiment shown, sterile bottle 10 contains the desired nutrient media. If nutrient media is to be added at a later date, it may be desired to add one more thermoplastic tube 20 and sterile connector 24 to the system so that the nutrient media may be provided to bottle 10 in a sterile manner.

After innoculation of the nutrient media in bottle 10 through one of the connected sterile connectors 24 and its thermoplastic tube 20, tube 20 may be transversely heat sealed in the conventional manner of blood banking technology, to seal off tube 20, prior to disconnection of its sterile connector 24 with the resultant contamination of the connector interior. The portion of tube 20 which is spaced from bottle 10 by the heat seal may be cut away for convenience of handling.

Thereafter, the innoculated bottle 10 may be incubated on a conventional roller bottle culturing apparatus for continuous agitating of the culture mixture under the desired conditions. The sealed system may exhibit adequate diffusion of oxygen into the system and carbon dioxide out of the system to promote good growth conditions for microoorganisms or cells with an aerobic metabolism.

At the conclusion of the culturing process, if it is desired to maintain sterile conditions, the other tubing 20 and its sterile connector 24 may be used to provide a sterile connection with another container for further processing or analysis as may be desired.

If the cultured cells/microorganisms need to be monitored for growth characteristics and/or biochemical evaluation of the media, the optional sample port can be used to take samples of the culture as required.

Because of the material used in the composition of the roller bottle it will not break or crack if dropped on the floor. This provides a safety margin when culturing highly infectious organisms or cell lines used for virology. A glass roller bottle, if dropped, would contaminate the work environment and possibly present a threat to the laboratory personnel.

The above has been offered for illustrative purposes only, and is not intended to limit the scope of the invention of this application, which is as defined in the claims below.

That which is claimed is:

1. A plastic culture bottle which comprises: a closed bottle defining a longitudinal axis and having flexible plastic walls; aseptically sealable means for access into said closed body; and a plurality of spaced reinforcement rings defined in said flexible plastic walls about said longitudinal axis, to cause said body to normally retain a predetermined, generally cylindrical shape, the flexible plastic walls being made of a plastic formulation and being of a thickness, at least apart from said rings, such that the rate of oxygen and carbon dioxide diffusion through said plastic walls is sufficient to permit the culturing of microorganisms and cells of aerobic metabolism.

2. A plastic bottle for suspension cultures, which comprises:
a closed body defining a longitudinal axis and having flexible plastic walls; aseptically sealable means for access into said closed body; and a plurality of spaced reinforcement rings defined in said flexible plastic walls about said longitudinal axis, to cause said body to normally retain a predetermined, generally cylindrical shape, the flexible plastic walls being made of a plastic formulation and being generally of a thickness, at least apart from said rings, such that an oxygen diffusion of at least 40 cc. and a carbon dioxide diffusion of at least 150 cc. is provided per square meter per hour through said plastic walls.

3. The bottle of claim 2 in which from 400 to 1000 square cm. of said plastic walls apart from said rings are present.

4. The bottle of claim 2 in which said access means comprises at least one flexible, thermoplastic access tube communicating through said closed body at one end thereof, said access tube having a free end which is sealed to sterile connector means.

5. The bottle of claim 2 which comprises from 10 to 40 percent by weight of a polyolefin consisting essentially of propylene units; from 40 to 85 percent by weight of a block copolymer, having thermoplastic rubber characteristics, consisting essentially of (1) a central block, comprising 50 to 85 percent by weight of the copolymer molecule, of a rubber olefin polymer of generally equal proportions of ethylene-butylene units, and (2) terminal blocks of polystyrene; and from 10 to 40 percent by weight of a softening agent comprising poly(ethylene-vinyl acetate) containing essentially from 28 to 35 percent by weight of vinyl acetate units, said plastic formulation being essentially free of liquid plasticizers.

6. The bottle of claim 5 in which the thickness of said plastic walls, apart from said rings, is from 0.012 to 0.04 inch.

7. The bottle of claim 2 which is proportioned to be usable in a roller-type culturing apparatus.

8. A plastic bottle for suspension cultures, which comprises:
a closed body defining a longitudinal axis and having flexible plastic walls; aseptically sealable means for access into said closed body; and a plurality of spaced reinforcement rings defined in said flexible plastic walls about said longitudinal axis, to cause said body to normally retain a predetermined, generally cylindrical shape, the flexible plastic walls being made of a plastic formulation and being generally of a thickness such that an oxygen diffusion of at least 40cc. and a carbon dioxide diffusion of at least 150cc. is provided per square meter per hour of said plastic walls, at least apart from said rings, there being from 400 to 1000 square centimeters of said plastic walls apart from said rings present, said aseptically sealable access means comprising at least one flexible, thermoplastic access tube communicating through said closed body at one end thereof, said access tube having a free end which is sealed to sterile connector means.

9. The bottle of claim 8 in which the thickness of said plastic walls, apart from said rings, is from 0.012 to 0.04 inch.

10. The bottle of claim 9 which comprises from 10 to 40 percent by weight of a polyolefin consisting essentially of propylene units; from 40 to 85 percent by weight of a block copolymer, having thermoplastic rubber characteristics, consisting essentially of (1) a central block, comprising 50 to 85 percent by weight of the copolymer molecule, of a rubbery olefin polymer of generally equal proportions of ethylene-butylene units, and (2) terminal blocks of polystyrene; and from 10 to 40 percent by weight of a softening agent comprising poly(ethylene-vinyl acetate) containing essentially from 28 to 35 percent by weight of vinyl acetate units, said plastic formulation being essentially free of liquid plasticizers.

11. The bottle of claim 10 which is proportioned to be usable in a roller-type culturing apparatus.

* * * * *